United States Patent [19]

Collington et al.

[11] Patent Number: 4,847,255

[45] Date of Patent: Jul. 11, 1989

[54] CYCLOPENTYL ETHERS AND THEIR USE IN MEDICINE

[75] Inventors: Eric W. Collington, Knebworth; Harry Finch, Letchworth; Duncan B. Judd, Ware; Malcolm Johnson, Orwell; Peter Strong, Stapleford, all of England

[73] Assignee: Glaxo Group Limited, London, England

[21] Appl. No.: 110,778

[22] Filed: Oct. 21, 1987

[30] Foreign Application Priority Data

Oct. 22, 1986 [GB] United Kingdom ............... 8625326

[51] Int. Cl.$^4$ ............... C07C 177/00; A61K 31/557; A61K 31/55
[52] U.S. Cl. ............... 514/212; 514/613; 514/708
[58] Field of Search ............... 514/212, 613, 708

[56] References Cited

U.S. PATENT DOCUMENTS

| | | | |
|---|---|---|---|
| 4,342,756 | 8/1982 | Collington et al. | 514/212 |
| 4,371,530 | 2/1983 | Collington et al. | 514/212 |
| 4,410,521 | 10/1983 | Collington et al. | 514/212 |
| 4,482,549 | 11/1984 | Collington et al. | 514/212 |
| 4,530,925 | 7/1985 | Collington et al. | 514/212 |
| 4,613,597 | 9/1986 | Collington et al. | 514/212 |

FOREIGN PATENT DOCUMENTS 0186181 12/1985 European Pat. Off. .

2174702 11/1986 United Kingdom .

OTHER PUBLICATIONS

Collington et al., Cyclopentyl Ethers and Their Preparation and Pharmaceutical Formulation, filed 9-14-87, U.S. Ser. No. 096,777, and filed 9-11-87, U.S. Ser. No. 097,344.

*Primary Examiner*—Ronald W. Griffin
*Attorney, Agent, or Firm*—Bernard, Rothwell & Brown

[57] ABSTRACT

The use is described of compounds of formula

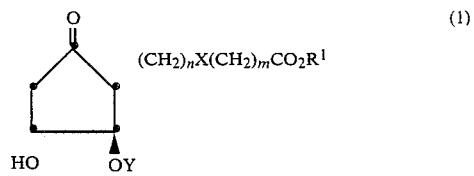

in which
n is 1 or 2;
m is 2–5 and X is —CH=CH— or —CH$_2$—CH$_2$—; or
m is 1–4 and X is —CH=CH=CH—;
R$^1$ is phenyl, substituted phenyl or naphthyl;
Y is substituted or unsubstituted 3-phenoxy-2-hydroxypropyl, in the therapy or prophylaxis of atherosclerosis and other disorders associated with abnormal levels of blood lipids and serum cholesterol.

20 Claims, No Drawings

CYCLOPENTYL ETHERS AND THEIR USE IN MEDICINE

This invention relates to new medical uses for certain chemical compounds and pharmaceutical compositions containing them. In particular, it relates to new uses for a group of cyclopentyl ethers in clinical conditions in which the underlying aetiology is associated with lipid imbalance or hyperlipidemia, and in the treatment of conditions were controlling levels of serum cholesterol would be beneficial.

In GB-A-2174702 we described a group of cyclopentyl ethers which have shown high potency and extended duration of action as regards the inhibition of gastric acid secretion and gastrointestinal cytoprotection and are therefore of interest in the treatment of ulcers. We have now found this same group of ethers have a potent lipid lowering action. The compounds are therefore of use in a variety of conditions where controlling non-esterified fatty acids and triglycerides and therefore lipoproteins and cholesterol would be beneficial. Examples of such conditions associated with lipid imbalance or abnormalities in lipid metabolism include hyperlipidemia, hypercholesterolemia, atherosclerosis, peripheral vascular disease and other cardiovascular conditions, and diabetes mellitus.

Thus according to one aspect of the invention we provide compounds of the general formula (1)

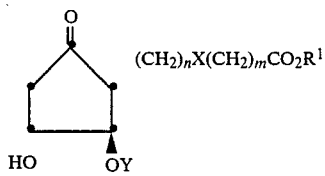

wherein
n is 1 or 2;
m is 2–5 and X is cis or trans —CH=CH— or —CH$_2$—CH$_2$—; or m is 1–4 and X is —CH=C=CH—;
R$^1$ is (a) phenyl [optionally substituted by C$_{1-4}$ alkyl, C$_{1-4}$ alkoxy, C$_{1-4}$ alkanoyl, methylthio, methylsulphinyl, methylsulphonyl, hologen (e.g. chlorine or bromine), —CO$_2$R$^2$[where R$^2$ is a hydrogen atom or C$_{1-4}$ alkyl or phenyl], —NHCOR$^2$[where R$^2$ is as defined above or is a phenyl group optionally substituted by hydroxyl, CH$_3$CONH— or

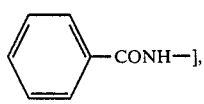

—CONR$^3$R$^4$ [where R$^3$ and R$^4$ may be the same or different and are each a hydrogen atom or C$_{1-4}$ alkyl group], —NHCONH$_2$, —CH$_2$CH(CONH$_2$)NHCOCH$_3$, or

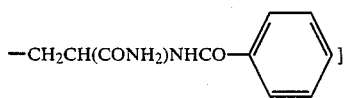

or
(b) 2-naphthyl;

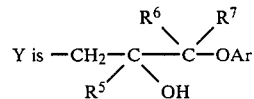

where R$^5$, R$^6$ and R$^7$ is each a hydrogen atom or a methyl group and at least one is a hydrogen atom; and
Ar is a phenyl group (optionally substituted by one or two C$_{1-4}$ alkyl, C$_{1-4}$ alkoxy. C$_{1-4}$ alkylthio, C$_{1-4}$ alkylsulphinyl, C$_{1-4}$ alkylsulphonyl, halogen or trifluoromethyl groups); and the physiologically acceptable salts thereof for use in the therapy or prophylaxis of atherosclerosis and other disorders associated with abnormal levels of blood lipids and serum cholesterol.

The structural formula herein are to be understood to include the enantiomers of each of the compounds concerned as well as mixtures of the enantiomers including racemates.

In general, the compounds of formula (1) in which the carbon atom carrying the group —(CH$_2$)$_n$X(CH$_2$)$_m$CO$_2$R$^1$ and/or the carbon atom in the group Y carrying the —OH group (particularly the former) are in the R-configuration and mixtures containing such isomers are preferred for use according to the invention.

The alkyl groups referred to above in the definition of the compounds of formula (1) may be straight or branched.

when R$^1$ in the compounds of formula (1) is phenyl substituted by a group —CO$_2$H the compounds are capable of salt formation with bases. Examples of suitable salts are alkali metal (e.g. sodium and potassium) salts.

Compounds of formula (1) in which the various substituents and groups have the meanings below are of particular use in all aspects of the invention.

Thus in compounds of formula (1) where X is —CH=CH— or —CH$_2$CH$_2$—, m is preferably 3 when n is 1, and m is preferably 2 or 4 when n is 2. When X is —CH=C=CH—, m is preferably 2 and n is 1, and is 1 or 3 when n is 2.

When X is —CH=CH— it is preferably cis —CH=CH—.

When R$^1$ is a substituted phenyl group it may be, for example, phenyl substituted in the meta, ortho or, in particular, para positions by a chlorine or bromine atom or a methyl, ethyl proply, n-butyl, t-butyl, methoxy, ethoxy, propoxy, butoxy, acetyl, propionyl, methylthio, methylsulphinyl, methylsulphonyl, —CO$_2$H, —CO$_2$CH$_3$,

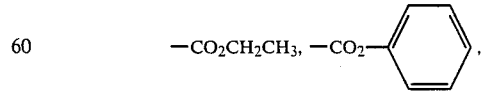

—NHCHO, —NHCOCH$_3$, benzoylamino, (acetylamino)benzoylamino, (hydroxy)benzoylamino, —CONH$_2$, —CONHCH$_3$ —CON(CH$_3$)$_2$, —CONHCH$_2$CH$_3$, —CON(CH$_2$CH$_3$)$_2$, —NHCONH$_2$, —CH$_2$CH(CONH$_2$)NHCOCH$_3$ or

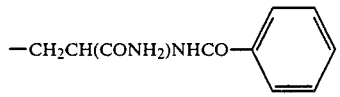

group.

Particularly useful substituents which may be present on a substituted phenyl group $R^1$ include $C_{1-4}$ alkoxy, $C_{1-4}$ alkanoyl, methylthio, methylsulphonyl, —$CO_2R^2$, —$NHCOR^2$, —$CONR^3R^4$ [where $R^2$, $R^3$ and $R^4$ are as defined for formula (J)], —$NHCONH_2$ or —$CH_2CH(CONH_2)NHCOCH_3$ groups. Especially useful substituents of this type include methoxy, acetyl, methylthio, methylsulphonyl, —$CO_2CH_3$, —$NHCOCH_3$, benzoylamino, (p-acetylamino)benzoylamino, (p-hydroxy)-benzoylamino, —$CONH_2$, —$CON(CH_3)_2$, —$NHCONH_2$ or —$CH_2CH(CONH_2)NHCOCH_3$.

The group $R^1$ is preferably a substituted phenyl group where the substituent may be in the meta, ortho or, in particular, para positions, or is a 2-naphthyl group.

Compounds in which $R^1$ is a phenyl group substituted (particularly in the para-position) by a methoxy, acetyl, —$CO_2CH_3$, —$NHCOCH_3$, benzoylamino, —$CONH_2$, —$CON(CH_3)_2$ or —$CH_2CH(CONH_2)NHCOCH_3$ group, or $R^1$ is a 2-naphthyl group, are particularly useful.

In the group Y, $R^6$ and $R^7$ are preferably hydrogen atoms.

When the Ar phenyl group is substituted, the substituent may be in the meta, ortho or para positions and may be for example methyl, ethyl, propyl, butyl, methoxy, ethoxy, propoxy, butoxy, methylthio, methylsulphinyl, methylsulphonyl, fluoro, chloro, bromo or trifluoromethyl. Preferably, only a single substituent is present, particularly at the para-position. In general, Ar is preferably phenyl or phenyl substituted by halogen, particularly fluoro or chloro.

The preferences indicated above apply both separately and in combination with one or more of the other stated preferences.

A preferred group of compounds for use according to the invention thus has the formula (1) in which:

X is cis—CH=CH— and n is 1 and m is 3 or n is 2 and m is 2 or 4, $R^1$ is a phenyl group substituted (preferably in the para-position) by a methoxy, acetyl, —$CO_2CH_3$ —$NHCOCH_3$, benzoylamino, —$CONH_2$, —$CON(CH_3)_2$ or —$CH_2CH(CONH_2)NHCOCH_3$ group or $R^1$ is a 2-naphthyl group;

$R^5$ is a hydrogen atom or a methyl group $R^6$ and $R^7$ are hydrogen atoms; and Ar is phenyl or phenyl substituted by fluoro or chloro.

Compounds of this type in which the carbon atom carrying the —$(CH_2)_nX(CH_2)_mCO_2R^1$ group is in the R-configuration are particularly preferred. Especially preferred compounds of this type are those which $R^1$ is a phenyl group substituted (preferably in the para-position) by benzoylamino.

An important group of compounds for use according to the invention are:

[1R-[1α(Z),2β(R*),3α]]-(-)-4-Acetylphenyl 7-[3-hydroxy-2-(2-hydroxy-3-phenoxypropoxy)-5-oxocylopentyl]-5-heptenoate;

[1R-[1α(Z),2β(R*),3α]]-(-)-4-(Acetylamino)phenyl 7-[3-hydroxy-2-(2-hydroxy-3-phenoxypropoxy)-5-oxocyclopentyl]-5-heptenoate;

[1R-[1α(Z),2β(R*),3α]]-(-)-4-(Bendzoylamino)phenyl 7-[3-hydroxy-2-(2-hydroxy-3-phenoxypropoxy)-5-oxocyclopentyl]-5-heptenoate;

[1R-[1α(Z),2≠β(R*),3α]]-(-)-4-[4-(Acetylamino)benzoylamino]phenyl 7-[3-hydroxy-2-(2-hydroxy-3-phenoxypropoxy)-5-oxocyclopentyl]-5-heptenoate;

[1R-[1α(Z),2β(R*),3α]]-(-)-4-(Aminocarbonyl)phenyl 7-[3-hydroxy-2-(2-hydroxy-3-phenoxypropoxy)-5-oxocyclopentyl]-5-heptenoate;

[1R-[1α(Z,S*),2β(R*),3α]]-(+)-4-[2-(Acetylamino)-3-amino-3-oxo propyl]phenyl 7-[3-hydroxy2-(2-hydroxy--3-phenoxypropoxy)-5oxocyclopentyl]-5-heptenoate;

[1R-[1α(Z),2β(R*),3α]]-(-)-3-(Benzoylamino)phenyl 7-[3-hydroxy-2-(2-hydroxy-3-phenoxypropoxy)-5-oxocyclopentyl]-5-heptenoate;

[1R-[1α(Z),2β(R*),3α]]-(-) Methyl 4-[[7-[3-hydroxy-2-(2-hydroxy-3-phenoxypropoxy)-5-oxocyclopentyl]1-oxo-5-heptenyl]oxy]-benzoate;

[1R-[1α(Z),2β(R*),3α]]-(-)-4-[4-(Hydroxy)benzoylamino]phenyl 7-[3-hydroxy-2-(2-hydroxy-3-phenoxypropoxy)-5-oxocyclopentyl]-5-heptenoate

[1R-[1α(Z),2β(R*),3α]]-2-Naphthalenyl 7-[3-hydroxy-2-(2-hydroxy-3-phenoxypropoxy)-5-oxocyclopentyl]-5-heptenoate;

[1R-[1α(Z),2β,3α]]-4-(Methylsulphonyl)phenyl 7-[3hydroxy-2-[2-hydroxy-3-[4-(methylthio)phenoxy]propoxy]-5-oxocyclopentyl]-5-heptenoate;

[1R-[1α(Z),2β(R*),3α]]-(-)-4-(Benzoylamino)phenyl 7-[3-hydroxy-2-(2-hydroxy-3-phenoxypropoxy)-5-oxocyclopentyl]-4-heptenoate;

[1R-[1α(Z),2β(R*),3α]]-(-)-4-(Benzoylamino)phenyl 9-[3-hydroxy-2-(2-hydroxy-3-phenoxypropoxy)-5-oxocyclopentyl]-7-nonenoate; and

[1R-[1α,2β(R*),3α]]-(-)-4-(Benzoylamino)phenyl 3-hydroxy-2-(2-hydroxy-3-phenoxypropoxy)-5-oxocyclopentaneheptanoate.

A particularly preferred compound for use according to the invention is [1R-[1α(Z),2β(R*),3α]]-(-)-4-(Benzoylamino)phenyl 7-[3-hydroxy-2-(2hydroxy-3-phenoxypropoxy)-5-oxocyclopentyl]-5-heptenoate.

Another particularly preferred compound for use according to the invention is [1R-[1α(Z),2β(R*),3α]]-(-)-4-(Benzoylamino)phenyl 7-[3-hydroxy-2-(2-hydroxy-3-phenoxypropoxy)-5-oxocyclopentyl]-4-heptenoate.

The efficacy of compounds of formula (1) in lowering liquid levels may be demonstrated in standard animal models, for example by determining their ability to lower non- esterified fatty acid and triglyceride levels in the starved rat (P. P. Lovisolo et. al., *Pharmacological Research Communications*, 1981, 13, 163–174; E. Shcillinger and O. Loge, *Biochemical Pharmacology*, 1974, 23, 2283–2289).

According to another aspect, the invention provides a method of treatment of a human or animal subject suffering from or susceptible to atherosclerosis or other diseases associated with lipid imbalance or abnormalities in lipid mechanism such as hyperlipdemia, hypercholesterolemia and other cardiovascular conditions, or a condition which may be relieved by controlling levels of serum lipids which comprises administering an effective amount of a compound of formula (1) or a physiologically acceptable salt thereof. Thus for example, the invention provides a method of treatment of a human subject suffering from or susceptible to atherosclerosis, or other diseases associated with lipid imbalance or abnormalities in lipid metabolism such as hyperlipidemia, hypercholesterolemia, peripheral vascular disease and other cardiovascular conditions, and diabetes mellitus.

According to a further aspect, the invention provides a pharmaceutical composition which comprises at least one compound of formula (1) or a physiologically acceptable salt thereof for use in human or veterinary medicine for the therapy or prophylaxis of atherosclerosis or other diseases associated with lipid imbalance or abnormalities in lipid metabolism such as hyperlipidemia, hypercholesterolemia, peripheral vascular disease and other cardiovascular conditions, and diabetes mellitus.

The compounds of formula (1) to be used according to the invention may be formulated in conventional manner, with one or more pharmaceutical carriers, for administration by any convenient route, for example for oral, buccal, parenteral or rectal administration.

The compounds of formula (1) may be formulated for oral administration as, for example, tablets, capsules, powders, solutions or syrups prepared by conventional means with acceptable excipients.

The compounds may be formulated for parenteral administration by bolus injections or continuous infusion. Formulations for injections may be presented in unit dosage form in ampoules, or in multi-dose containers, with an added preservative.

For buccal administration, the compounds may be formulated as tablets or lozenges in conventional manner; and for rectal administration compositions such as suppositories or retention enemas, for example containing conventional suppository bases such as cocoa butter or other glyceride, can be used.

The compounds may be administered orally, for example in amounts of 0.1 to 500µg/kg body weight, preferably 0.1 to 100µg/kg body weight, 1 to 4 times daily. For parenteral administration, the compounds may be administered in amounts of 0.01 to 100µg/kg body weight, 1 to 4 times daily. The precise dose will of course depend on the age and condition of the patient.

According to a further aspect, the invention provides a compound of formula (1) or a physiologically acceptable salt thereof for use in the manufacture of a medicament for the therapy or prophylaxis of atherosclerosis or other diseases associated with lipid imbalance or abnormalities in lipid metabolism such as hyperlipidemia, hypercholesterolemia, peripheral vascular disease and other cardiovascular conditions, and diabetes mellitus.

The compounds of general formula (1) and their salts may be prepared according to the methods described in GB-A-2174702.

The following are examples of pharmaceutical formulations for use according to the invention. In the examples, the term "active ingredient" is used to denote a compound of the invention, and may in particular be a compound [1R-[1α(Z),2β(R*),3α]]-(-)-4-(benzoylamino)phenyl 7-[3-hydroxy-2-(2-hydroxy-3-phenoxypropaxy)-5-oxocyclopentyl]-5-heptenoate or [1R-[1α(Z),2β(R*),3α]]-(-)-4-(benzoylamino)phenyl 7-[3-hydroxy-2-(2-hydroxy-3-phenoxypropoxy)-5-oxocyclopentyl]-4-heptenoate.

| 1. Tablets These may be prepared by direct compression | |
|---|---|
| | mg/tablet |
| Active Ingredient | 0.015 to 0.2 |
| Magnesium stearate, BP | 1.5 |
| Microcrystalline cellulose, USP to compression weight | 150.0 |

The active ingredient is blended with about 10% of the microcrystalline cellulose then blended with the remaining mircocrystalline cellulose and magnesium stearate. The blend is then compressed using 6 mm diameter punches into tablets on a suitable machine.

The tablets may be film coated with suitable film forming materials e.g. methyl cellulose or hydroxypropyl methylcellulose using standard techniques.

| 2. Capsules | |
|---|---|
| | mg/tablet |
| Active ingredient | 0.015 to 0.2 |
| Magnesium stearate, BP | 1.0 |
| *Starch 1500 to fill weight | 100.0 |

*A form of directly compressible starch.

The active ingredient is preblended with some of the Starch 1500 then this preblend is mixed with the remaining Starch 1500 and magnesium stearate. The mix is then filled into size No. 2 hard gelatin capsule shells using suitable machinery.

We claim:

1. A method for the therapy or prophylaxis of atherosclerosis and other disorders associated with abnormal levels of blood lipids and serum cholesterol, which comprises administering to a patient a therapeutically effective amount of

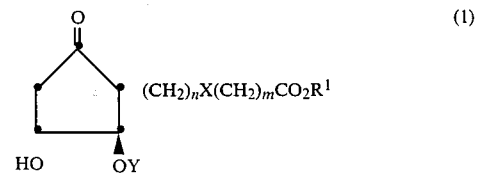

wherein
n is 1 or 2;
m is 2–5 and X is cis or trans —CH=CH— or —CH₂—CH₂—; or m is 1–4 and X is —CH=C=CH—;
R¹ is selected from the group consisting of phenyl, phenyl substituted by a substituent selected from the group consisting of $C_{1-4}$ alkoxy, $C_{1-4}$ alkanoyl, methylthio, methylsulphinyl, methylsulphonyl, halogen, —CO₂R² (where R² is a hydrogen atom or $C_{1-4}$ alkyl or phenyl), —NHCOR² (where R² is selected from the group consisting of a hydrogen atom, $C_{1-4}$ alkyl, phenyl, or a phenyl group substituted by a substituent selected from the group consisting of hydroxyl, CH₃CONH—) or

—CONR³R⁴ (where R³ and R⁴ may be the same or different and are each a hydrogen atom or $C_{1-4}$ alkyl group), —NHCONH₂, —CH₂CH(CONH₂)NH-COCH₃, or —CH₂CH(CONH₂)

or 2-naphthyl;

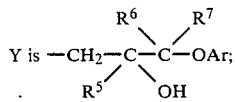

where R⁵, R⁶ and R⁷ is each a hydrogen atom or a methyl group and at least one is a hydrogen atom; and
Ar is selected from the group consisting of a phenyl group, substituted phenyl wherein said substituent is selected from the group consisting of one or two $C_{1-4}$ alkyl, $C_{1-4}$ alkoxy, $C_{1-4}$ alkylthio, $C_{1-4}$ alkylsulphinyl, $C_{1-4}$ alkylsulphonyl, halogen or trifluoromethyl groups, or a physiologically acceptable salt thereof.

2. A method as claimed in claim 1 for the therapy or prophylaxis of atherosclerosis, hyperlipidemia, hypercholesterolemia, peripheral vascular disease and other cardiovascular conditions, and diabetes mellitus.

3. A method as claimed in claim 1 in which, in the compound of formula (1), X is —CH=CH— or —CH₂—CH₂— and m is 3 when n is 1 and m is 2 or 4 when n is 2; or X is —CH=C=CH— and m is 2 when n is 1 and m is 1 or 3 when n is 2.

4. A method as claimed in claim 1 in which, in the compound of formula (1), R¹ is phenyl substituted by a methoxy, acetyl, —CO₂CH₃, —NHCOCH₃, benzoylamino, —CONH₂, —CON(CH₃)₂ or —CH₂CH(CONH₂)NHCOCH₃ group, or R¹ is a 2-naphthyl group.

5. A method as claimed in claim 1 in which, in the compound of formula (1), R⁶ and R⁷ are hydrogen atoms and Ar is phenyl or phenyl substituted by fluoro or chloro.

6. A method as claimed in claim 1 in which, the compound of formula (1):
X is cis—CH=CH— and n is 1 and m is 3 or n is 2 and m is 2 or 4;
R¹ is a phenyl group substituted by a methoxy, acetyl, —CO₂CH₃, —NHCOCH₃, benzoylamino, —CONH₂, —CON(CH₃)₂ or —CH₂CH(CONH₂)NHCOCH₃ group or R¹ is a 2-naphthyl group;
R⁵ is a hydrogen atom or a methyl group;
R⁶ and R⁷ are hydrogen atoms; and
Ar is phenyl or phenyl substituted by fluoro or chloro.

7. A method as claimed in claim 1 in which, in the compound of formula (1), the carbon atom carrying the group —(CH₂)ₙX(CH₂)ₘCO₂R¹ is in the R-configuration.

8. A method as claimed in claim 1 in which the compound of formula (1) is:
[1R-[1α(Z),2β(R*),3α]]-(-)-4-(benzoylamino)phenyl 7-[3-hydroxy-2-(2-hydroxy-3-phenoxypropoxy)-5-oxocyclopentyl]-5-heptenoate.

9. A method as claimed in claim 1 in which the compound of formula (1) is:
[1R-[1α(Z),2β(R*),3α]]-(-)-4-(benzoylamino)phenyl 7-[3-hydroxy-2-(2-hydroxy-3-phenoxypropoxy)-5-oxocyclopentyl]-4heptenoate.

10. A method as claimed in claim 1 in which the compound of formula (1) is presented in the form of a tablet or capsule.

11. A method as claimed in claim 8 for the therapy or prophylaxis of atherosclerosis.

12. A method as claimed in claim 9 for the therapy or prophylaxis of atherosclerosis.

13. A method for the therapy or prophylaxis of atherosclerosis and other disorders associated with abnormal levels of blood lipids and serum cholesterol, which comprises administering a compound of the general formula (1)

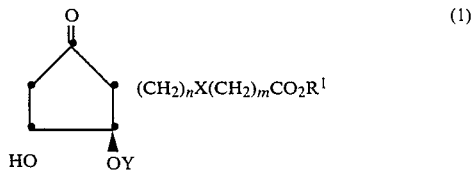

wherein
X is cis—CH=CH— and n is 1 and m is 3 or n is 2 and m is 2 or 4;

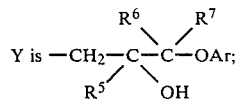

R¹ is a phenyl group substituted by a methoxy, acetyl, —CO₂CH₃, —NHCOCH₃, benzoylamino, —CONH₂, —CON(CH₃)₂ or —CH₂CH(CONH₂)NHCOCH₃ group or R¹ is a 2-naphthyl group;
R⁵ is a hydrogen atom or a methyl group;
R⁶ and R⁷ are hydrogen atoms; and
Ar is phenyl or phenyl substituted by floro or chloro.

14. A method as claimed in claim 13 for the therapy or prophylaxis of atherosclerosis, hyperlipidemia, hypercholesterolemia, peripheral vascular disease and other cardiovascular conditions, and diabetes mellitus.

15. A method as claimed in claim 13 in which, in the compound of formula (1), the carbon atom carrying the group —(CH₂)ₙX(CH₂)ₘCO₂R¹ is in the R-configuration.

16. A method as claimed in claim 13 in which the compound of formula (1) is:
[1R-[1α(Z),2β(R*),3α]]-(-)-4-(benzoylamino)phenyl 7-[3-hydroxy-2-(2-hydroxy-3-phenoxypropoxy)-5-oxocyclopentyl]-5-heptenoate.

17. A method as claimed in claim 13 in which the compound of formula (1) is:
[1R-[1α(Z),2β(R*),3α]]-(-)-4-(benzoylamino)phenyl 7-[3-hydroxy-2-(2-hydroxy-3-phenoxypropoxy)-5-oxocyclopentyl]-4-heptenoate.

18. A method as claimed in claim 13 in which the compound of formula (1) is presented in the form of a tablet or capsule.

19. A method as claimed in claim 16, for the therapy or prophylaxis of atherosclerosis.

20. A method as claimed in claim 17, for the therapy or prophylaxis of atherosclerosis.

* * * * *